United States Patent
Burbank et al.

(10) Patent No.: US 9,388,059 B2
(45) Date of Patent: Jul. 12, 2016

(54) FILTRATION SYSTEM FOR PREPARATION OF FLUIDS FOR MEDICAL APPLICATIONS

(71) Applicant: NxStage Medical, Inc., Lawrence, MA (US)

(72) Inventors: Jeffrey H. Burbank, Boxford, MA (US); Dennis M. Treu, Castle Rock, CO (US); Christopher S. McDowell, Holladay, UT (US); Goetz Friederichs, Boston, MA (US)

(73) Assignee: NXSTAGE MEDICAL, INC., Lawrence, MA (US)

( * ) Notice: Subject to any disclaimer, the term of this patent is extended or adjusted under 35 U.S.C. 154(b) by 301 days.

(21) Appl. No.: 13/968,430

(22) Filed: Aug. 16, 2013

(65) Prior Publication Data

US 2013/0327691 A1 Dec. 12, 2013

Related U.S. Application Data

(60) Division of application No. 13/603,505, filed on Sep. 5, 2012, now Pat. No. 8,545,428, which is a division of application No. 13/083,915, filed on Apr. 11, 2011, now Pat. No. 8,679,348, which is a continuation of application No. 10/585,675, filed as application No. PCT/US2005/000381 on Jan. 7, 2005, now abandoned.

(30) Foreign Application Priority Data

Jan. 7, 2004 (WO) ................ PCT/US2004/000476

(51) Int. Cl.
*C02F 1/44* (2006.01)
*A61M 1/14* (2006.01)
(Continued)

(52) U.S. Cl.
CPC .. *C02F 1/44* (2013.01); *A61M 1/14* (2013.01); *A61M 1/1656* (2013.01); *A61M 1/3462* (2013.01); *A61M 2205/12* (2013.01)

(58) Field of Classification Search
None
See application file for complete search history.

(56) References Cited

U.S. PATENT DOCUMENTS 2,995,334 A 8/1961 Henderson et al.
3,034,085 A 5/1962 Pauler et al.
(Continued)

FOREIGN PATENT DOCUMENTS

DE 8305713 12/1985
DE 19704564 8/1998
(Continued)

OTHER PUBLICATIONS

FDA guidelines for Bacterial Endotoxins/Pyrogens. Accessed Apr. 12, 2010. http://www.fda.gov/ICECl/Inspections/InspectionGuides/InspectionTechnical- Guides/ucm072918.htm.
(Continued)

*Primary Examiner* — Krishnan S Menon
(74) *Attorney, Agent, or Firm* — Potomac Law Group, PLLC

(57) ABSTRACT

Systems, methods, and devices for preparation of water for various uses including blood treatment are described. In embodiments, fluid is passed through a first filtration step which is effective for creating purified water and a pair of ultrafilters placed at the outlet. The ultrafilters are separated by an intervening flow path to prevent grow-through from the outlet end upstream. In embodiments, a recirculation path with an air removing filter helps to eliminate air from the ultimate product water.

11 Claims, 8 Drawing Sheets

(51) Int. Cl.
*A61M 1/16* (2006.01)
*A61M 1/34* (2006.01)

(56) References Cited

U.S. PATENT DOCUMENTS

| | | | |
|---|---|---|---|
| 3,100,486 A | 8/1963 | Nehring | |
| 3,103,335 A | 9/1963 | Martinez | |
| 3,252,124 A | 5/1966 | Hansen | |
| 3,709,365 A | 1/1973 | Czaplinski et al. | |
| 4,059,512 A | 11/1977 | Harris | |
| 4,144,884 A | 3/1979 | Tersteegen et al. | |
| 4,202,332 A | 5/1980 | Tersteegen et al. | |
| 4,246,101 A | 1/1981 | Selby, III | |
| 4,370,983 A | 2/1983 | Lichtenstein | |
| 4,431,545 A * | 2/1984 | Pall et al. | 210/641 |
| 4,432,765 A | 2/1984 | Oscarsson | |
| 4,495,067 A | 1/1985 | Klein et al. | |
| 4,564,132 A | 1/1986 | Lloyd-Davies | |
| 4,596,550 A | 6/1986 | Troutner | |
| 4,623,450 A | 11/1986 | Vantard et al. | |
| 4,626,240 A | 12/1986 | Edelman et al. | |
| 4,643,389 A | 2/1987 | Elson et al. | |
| 4,661,246 A | 4/1987 | Ash | |
| 4,702,829 A * | 10/1987 | Polaschegg et al. | 210/195.2 |
| 4,711,715 A | 12/1987 | Polaschegg | |
| 4,753,371 A | 6/1988 | Michielin et al. | |
| 4,772,390 A * | 9/1988 | Kawai et al. | 210/651 |
| 4,784,495 A | 11/1988 | Jonsson et al. | |
| 4,784,768 A * | 11/1988 | Mathieu | 210/321.8 |
| 5,032,265 A | 7/1991 | Jha et al. | |
| 5,079,236 A | 1/1992 | Drizen et al. | |
| 5,102,399 A | 4/1992 | Chu | |
| 5,139,483 A | 8/1992 | Ryan | |
| 5,221,483 A | 6/1993 | Glenn et al. | |
| 5,259,954 A | 11/1993 | Taylor | |
| 5,308,333 A | 5/1994 | Skakoon | |
| 5,368,555 A | 11/1994 | Sussman et al. | |
| 5,423,768 A | 6/1995 | Folden et al. | |
| 5,484,431 A | 1/1996 | Scharf et al. | |
| 5,536,412 A | 7/1996 | Ash | |
| 5,591,344 A | 1/1997 | Kenley et al. | |
| 5,622,626 A | 4/1997 | Matkovich et al. | |
| 5,645,734 A | 7/1997 | Kenley et al. | |
| 5,662,642 A | 9/1997 | Isono et al. | |
| 5,690,831 A | 11/1997 | Kenley et al. | |
| 5,702,597 A | 12/1997 | Chevallet et al. | |
| 5,707,038 A | 1/1998 | Cocatre-Zilgien | |
| 5,779,905 A | 7/1998 | Morandi et al. | |
| 5,782,762 A | 7/1998 | Vining | |
| 5,919,357 A | 7/1999 | Wilkins et al. | |
| 5,951,863 A | 9/1999 | Kruger et al. | |
| 5,972,225 A | 10/1999 | Karras et al. | |
| 6,039,877 A | 3/2000 | Chevallet et al. | |
| 6,044,691 A | 4/2000 | Kenley et al. | |
| 6,106,723 A | 8/2000 | Grandics et al. | |
| 6,132,616 A | 10/2000 | Twardowski et al. | |
| 6,136,201 A | 10/2000 | Shah et al. | |
| 6,146,536 A | 11/2000 | Twardowski | |
| 6,187,207 B1 | 2/2001 | Brauer | |
| 6,253,567 B1 | 7/2001 | Imanari et al. | |
| 6,254,567 B1 | 7/2001 | Treu et al. | |
| 6,284,142 B1 | 9/2001 | Muller | |
| 6,287,516 B1 | 9/2001 | Matson et al. | |
| 6,331,252 B1 | 12/2001 | El Sayyid et al. | |
| 6,428,518 B1 | 8/2002 | Brengle et al. | |
| 6,475,385 B1 | 11/2002 | Boyce et al. | |
| 6,485,649 B1 | 11/2002 | Terava et al. | |
| 6,561,997 B1 | 5/2003 | Weitzel et al. | |
| 6,572,576 B2 | 6/2003 | Brugger et al. | |
| 6,579,253 B1 | 6/2003 | Burbank et al. | |
| 6,582,385 B2 | 6/2003 | Burbank et al. | |
| 6,589,482 B1 | 7/2003 | Burbank et al. | |
| 6,595,943 B1 | 7/2003 | Burbank | |
| 6,607,697 B1 | 8/2003 | Muller | |
| 6,626,857 B1 | 9/2003 | Ohta et al. | |
| 6,638,477 B1 | 10/2003 | Treu et al. | |
| 6,638,478 B1 | 10/2003 | Treu et al. | |
| 6,649,063 B2 | 11/2003 | Brugger et al. | |
| 6,691,058 B2 | 2/2004 | Blakley | |
| 6,743,193 B2 | 6/2004 | Brugger et al. | |
| 6,745,903 B2 | 6/2004 | Grandics | |
| 6,830,553 B1 | 12/2004 | Burbank et al. | |
| 6,852,090 B2 | 2/2005 | Burbank et al. | |
| 6,855,122 B1 | 2/2005 | Ohta et al. | |
| 6,955,655 B2 | 10/2005 | Burbank et al. | |
| 6,962,575 B2 | 11/2005 | Tal | |
| 6,982,038 B2 | 1/2006 | Dolecek et al. | |
| 7,214,312 B2 | 5/2007 | Brugger et al. | |
| 7,226,538 B2 | 6/2007 | Brugger et al. | |
| 7,322,969 B2 | 1/2008 | Hattori et al. | |
| 7,419,597 B2 | 9/2008 | Brugger et al. | |
| 7,473,238 B2 | 1/2009 | Brugger et al. | |
| 7,544,300 B2 | 6/2009 | Brugger et al. | |
| 2001/0016699 A1 | 8/2001 | Burbank et al. | |
| 2001/0021817 A1 | 9/2001 | Brugger et al. | |
| 2001/0037079 A1 | 11/2001 | Burbank et al. | |
| 2001/0039441 A1 | 11/2001 | Ash | |
| 2001/0048909 A1 | 12/2001 | Taylor | |
| 2002/0085952 A1 | 7/2002 | Ellingboe et al. | |
| 2002/0104800 A1 | 8/2002 | Collins et al. | |
| 2002/0167322 A1 | 11/2002 | He et al. | |
| 2002/0190000 A1 | 12/2002 | Baurmeister | |
| 2003/0010701 A1 | 1/2003 | Collins et al. | |
| 2003/0010717 A1 | 1/2003 | Brugger et al. | |
| 2003/0010719 A1 | 1/2003 | Brugger et al. | |
| 2003/0042201 A1 | 3/2003 | Sizelove et al. | |
| 2003/0051767 A1 | 3/2003 | Coccaro et al. | |
| 2003/0080140 A1 | 5/2003 | Neas et al. | |
| 2003/0105435 A1 | 6/2003 | Taylor | |
| 2003/0130606 A1 | 7/2003 | Tuck | |
| 2003/0168389 A1 | 9/2003 | Astle et al. | |
| 2003/0173297 A1 | 9/2003 | Grandics | |
| 2003/0236481 A1 | 12/2003 | Burbank | |
| 2004/0045881 A1 | 3/2004 | Collins et al. | |
| 2004/0060866 A1 | 4/2004 | Radunsky et al. | |
| 2004/0069709 A1 | 4/2004 | Brugger et al. | |
| 2004/0089594 A1 | 5/2004 | Collins et al. | |
| 2004/0186415 A1 | 9/2004 | Burbank et al. | |
| 2004/0222139 A1 | 11/2004 | Brugger et al. | |
| 2004/0232079 A1 | 11/2004 | Taylor et al. | |
| 2005/0045548 A1 | 3/2005 | Brugger et al. | |
| 2005/0103717 A1 | 5/2005 | Jha et al. | |
| 2005/0171501 A1 | 8/2005 | Kelly | |
| 2005/0209547 A1 | 9/2005 | Burbank et al. | |
| 2005/0215975 A1 | 9/2005 | Mathias et al. | |
| 2006/0021944 A1 | 2/2006 | Carson et al. | |
| 2007/0007208 A1 | 1/2007 | Brugger et al. | |
| 2007/0038191 A1 | 2/2007 | Burbank et al. | |
| 2007/0260168 A1 | 11/2007 | Brugger et al. | |
| 2008/0053905 A9 | 3/2008 | Brugger et al. | |
| 2008/0173574 A1 | 7/2008 | Silveri | |
| 2008/0203023 A1 | 8/2008 | Burbank et al. | |
| 2008/0230450 A1 | 9/2008 | Burbank et al. | |

FOREIGN PATENT DOCUMENTS

| | | |
|---|---|---|
| GB | 2135598 | 9/1984 |
| JP | 49-041276 | 11/1974 |
| JP | 57-211362 | 12/1982 |
| JP | 2003-175101 | 6/2003 |
| JP | 2004-000583 | 1/2004 |
| WO | WO 96/36370 | 11/1996 |
| WO | WO 99/56696 | 11/1999 |
| WO | WO 02/32476 | 4/2002 |
| WO | WO 02/095675 | 11/2002 |
| WO | WO 03/006100 | 1/2003 |
| WO | WO 03/006139 | 1/2003 |
| WO | WO 03/103533 | 12/2003 |
| WO | WO 2004/062710 | 7/2004 |
| WO | WO 2004/066121 | 8/2004 |
| WO | WO 2004/080282 | 9/2004 |
| WO | WO 2004/084972 | 10/2004 |

(56) References Cited

FOREIGN PATENT DOCUMENTS

| WO | WO 2005/068043 | 7/2005 |
| WO | WO 2006/074429 | 7/2006 |
| WO | WO 2007/118235 | 10/2007 |

OTHER PUBLICATIONS

Ledebo, Ingrid, "On-line Preparation of Solutions for Dialysis: Practical Aspects Versus Safety and Regulations." *Journal of the American Society of Nephrology*, 2002, 13: pp. S78-S83.

Online encyclopedia article "Depyrogenation." Accessed Apr. 12, 2010. http://en.wikipedia.org/wiki/Depyrogenation.

"Operator's Manual, Fresenius 2008H Hemodialysis Machine," p. 135. Accessed Jun. 24, 2012. http://www.fmcna.com/documents/2008H_Op_Manual_RevH.pdf.

"Risk Free Connection of Pre-Sterilized Single Use Fluid Path Assemblies to Stainless Steel SIP Systems with Lynx ST (Steam-to) Connectors." Millipore Corporation Catalog, May 2003.

Snipe, Brad, "The Case for UV in Dechlorination Applications." Water Conditioning and Purification Magazine, vol. 45, No. 1, Jan. 2003.

\* cited by examiner

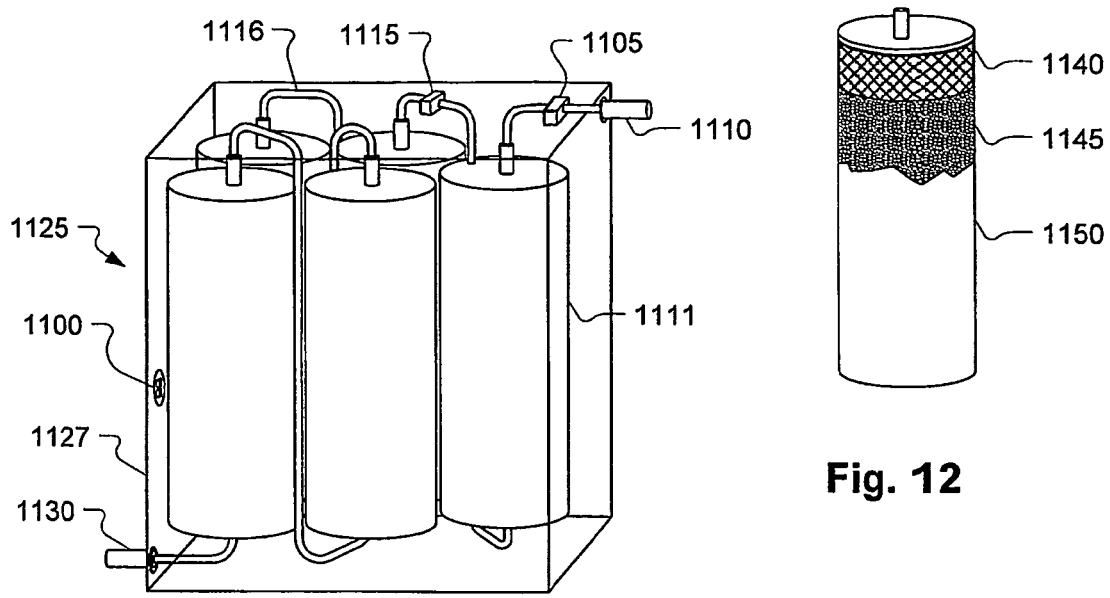
Fig. 11
Fig. 12
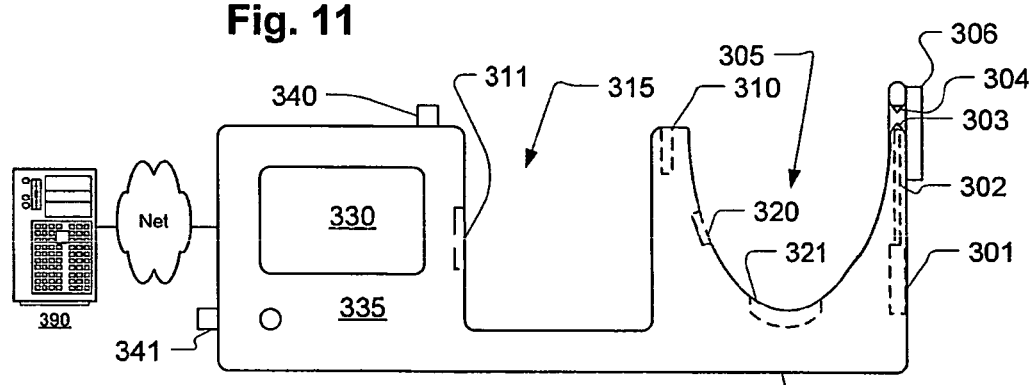
Fig. 13A
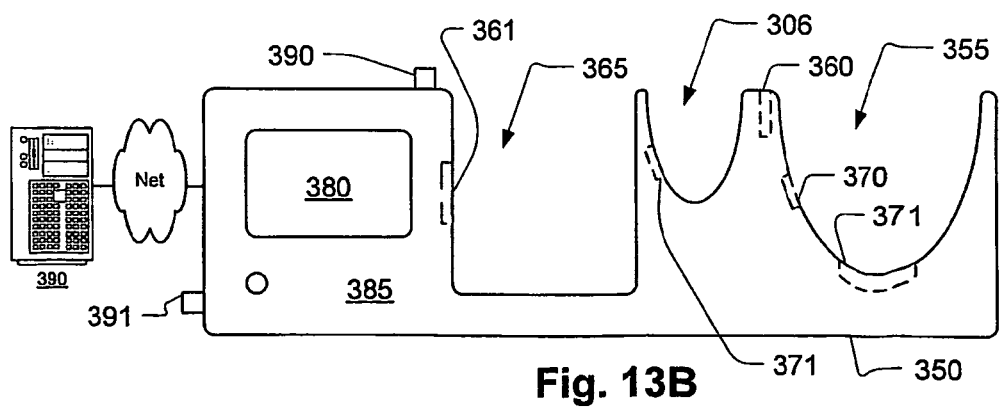
Fig. 13B

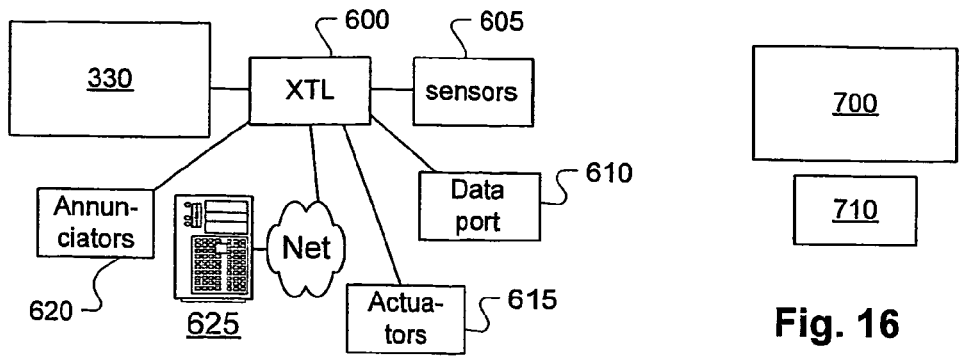
Fig. 14
Fig. 16
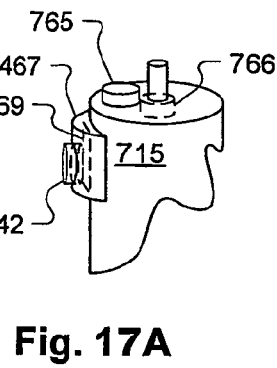
Fig. 17A
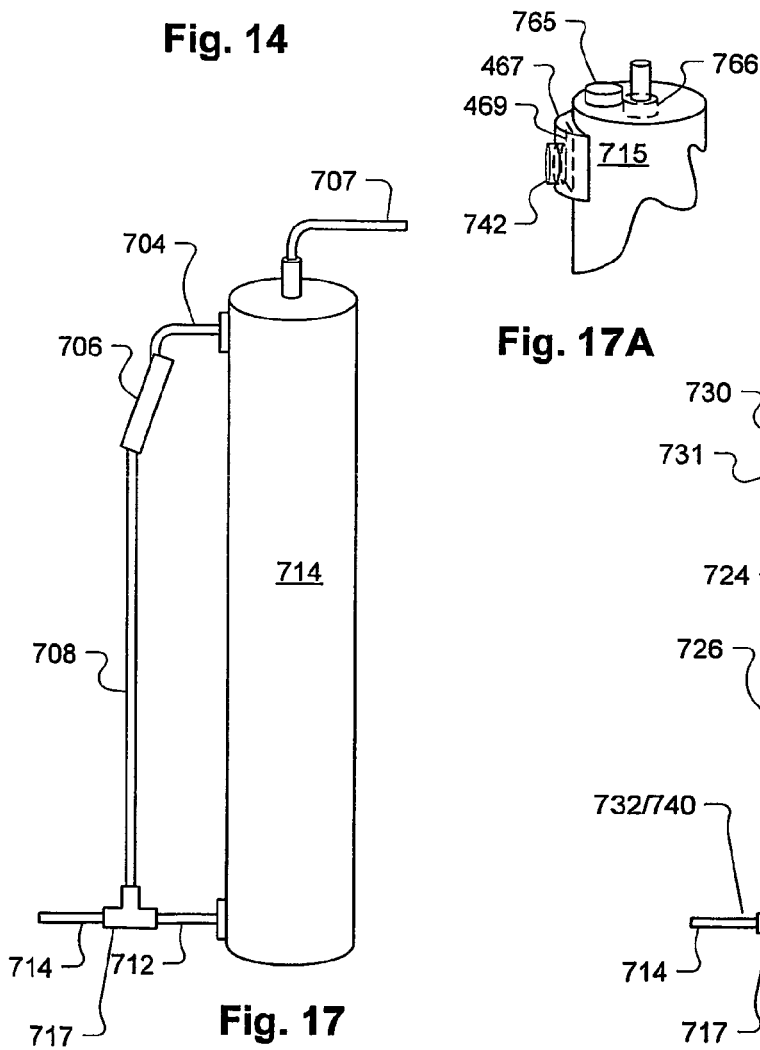
Fig. 17
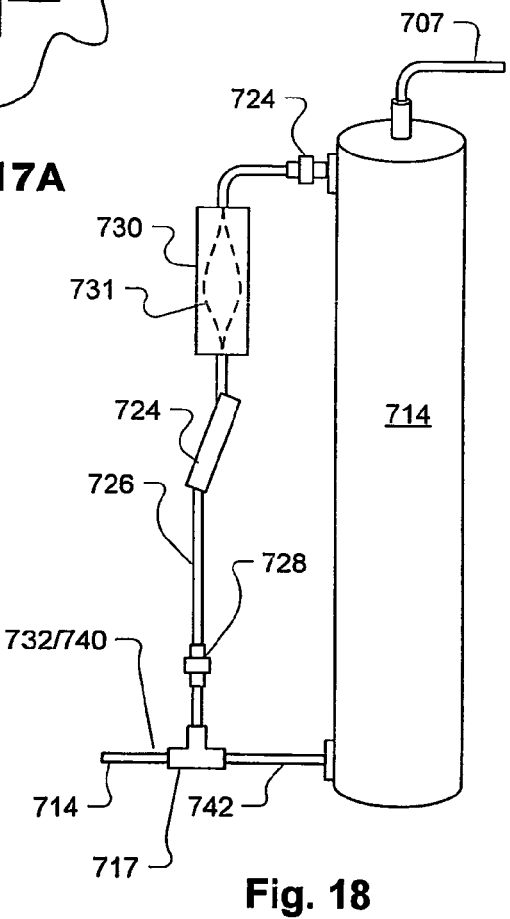
Fig. 18

FILTRATION SYSTEM FOR PREPARATION OF FLUIDS FOR MEDICAL APPLICATIONS

BACKGROUND OF THE INVENTION

Many medical applications require purified water and other fluids. for example, hemofiltration, tissue irrigation, and hemodiafiltration. Some prior art systems have focused on continuous purification processes that require a separate dfiltration/purification apparatus that must be periodically purged and verified to provide sufficient constant flow of sterile replacement fluid. (See Chavallet U.S. Pat. Nos. 6,039, 877 and 5,702,597.) Such devices are necessarily complicated and require separate pumping systems for the purification process. In addition, the rate of supply of fluid for such systems is very high, requiring expensive filters to be used. The same high-rate problem exists for the generation of replacement fluid for hemofiltration, and therefore also requires expensive filtering apparatus.

Large and small scale inline systems are known for preparation of infusible fluids and for preparation of dialysate. The following prior art references discuss examples of such systems.

US Patent Publication No. 2004/0232079
US Patent Publication No. 2003/0105435
U.S. Pat. No. 5,645,734
U.S. Pat. No. 5,782,762
U.S. Pat. No. 6,136,201
PURELAB Maxima, Ultra-Pure Water Purification Systems
Shipe, Brad; "The Case for UV in Dechlorination Applications,"Water Conditioning & Purification Magazine, January 2003, Vol 45 No. 1.

BRIEF DESCRIPTION OF THE DRAWINGS

FIG. 11 illustrates a filter module in partial ghost perspective view.

FIG. 12 illustrates a filter cartridge with an expansion device.

FIGS. 13A and 13B illustrate fluid preparation devices for use with a replaceable filter module such as the one illustrated in FIG. 11.

FIG. 14 illustrates a control system to support features of various embodiments.

FIG. 16 illustrates a treatment environment for use of a control embodiment.

FIGS. 17, 17A, and 18 illustrate ultrafilter configurations that are tolerant of the evolution of air from within the ultrafilter.

DETAILED DESCRIPTION

The present disclosure relates to apparatus, methods, devices, articles of manufacture, etc. for producing pure water and, in some embodiments, pure solutions. These may be used for the preparation of solutions for medical applications such as tissue irrigation, preparation of pharmaceutical, blood treatments such as hemofiltration, hemodialysis, hemodiafiltration and ultrafiltration, and other treatments.

Figure 1A:
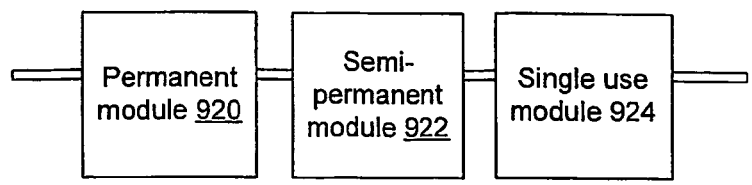
FIG. 1A illustrates a fluid preparation apparatus embodiments in a figurative way for discussing various features and arrangements of a medical fluid purification system.

As described in FIG. 1A, to supply suitable water that is substantially free of unwanted dissolved and undissolved materials, a combination of permanent and replaceable components may be provided at the treatment site. FIG. 1A is an overview of a framework that provides benefits, particularly in certain environments. One such environment is renal replacement therapy. Patients must be treated at least twice a week and often daily. On the other hand, excellent sterility design urges the use of pre-sterilized throw-away components to ensure against various modes of contamination which need not be enumerated. But replacing every component that must be contamination-free upon every use is profoundly expensive, particularly where treatments are done every day. Prior art approaches have addressed this problem by combining permanent components whose sterility is guaranteed by intensive sterilization procedures, some of which are backed up (made failsafe) by using additional disposable components that are used once and discarded. Alternatively, the disposable can be made more robust to avoid the on-site sterilization procedures. But this presents the problem of forcing the designer to use inexpensive, and therefore less desirable components in the disposable portions, or of simply imposing the burden of high cost on the medical treatment system.

FIG. 1A shows a new model that compromises on this point and is considered particularly applicable in the renal replacement therapy environment. A permanent module 920 has certain pretreatment components that may be used repeatedly without replacement and without sterilization and includes filtration and treatment steps that are not unduly inclined to aggravate, or susceptible to, contamination. Examples are illustrated in the further embodiments. This permanent module may be designed to receive variations of water quality. A semi-permanent module 922 provides more than one use, for example a month's worth of uses, but is disposable periodically or upon detection of incipient failure. The permanent module may contain a controller to enforce the proper use and handling of the semi-permanent module since safeguards must be enforced with regard to it. But with the semi-permanent modules, as discussed below in connection with particular embodiments, the procedures do not involve washing, cleansing, sterilization. The final stage includes final filtration and/or treatment steps provided in a single-use element 924. In the final stage, the least expensive components may be arranged to guard against sterility failures of the upstream components. As will be seen, the preferred embodiments described herein conform to this model. Variations of the model are possible including fragmenting the intermediate modules into ones used according to other schedules such as one module replaced monthly and another replaced weekly.

Figure 1B:
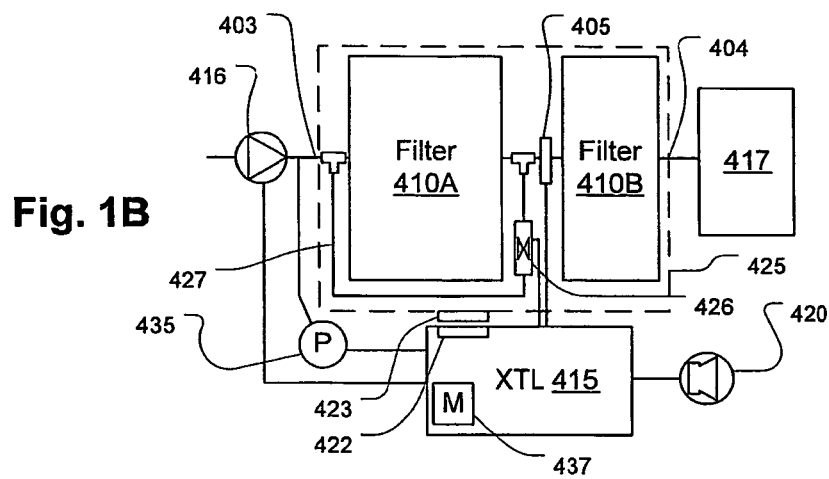
FIG. 1B illustrates a filter device with control elements that provide assurance of fluid quality and prevent breakthrough of contamination upon filter expiration.

An example of a semi-permanent element and a control system to safeguard against contamination are shown in FIG. 1B. Note that the embodiment of FIG. 1B may constitute an independent invention and need not be employed in a combination as discussed with reference to FIG. 1A, although this is identified as a preferred configuration. Referring to FIG. 1B, a pump 416 feeds raw water into a filter module 425 via an input line 403. The filter module 425 contains first and second filters 410A and 410B. In an embodiment, the first and second filter stages 410A and 410B are deionizing filters. The first and second filter stages 410A and 410B may be accompanied by other types of filters (not shown here but discussed and illustrated elsewhere in the instant specification) in the filter module or externally thereto to perform a complete water treatment. Treated water is supplied to a batch container 417, which may or may not be present. In the illustrated configuration, water is treated for preparation of a medicament which may be included in concentrate form in the batch container 417 as a presterilized consumable unit.

Between the first and second filter stages 410A and 410B, a water quality sensor 405 is provided. In an embodiment, the water quality sensor 405 is a conductivity or resistivity probe that detects ionic species in the water after passing through the first stage filter 410A. In a preferred embodiment, the second stage 410B provides at least some redundancy in that the second stage 4108 provides some of the filtration effect of the first stage 410A. In an alternative embodiment it provides all of the filtration of the first stage 410A and is thereby completely redundant. In such an arrangement, the first stage would expire (become depleted), allowing contaminants to break through, before the second stage expires. The contaminant breakthrough is detected by a controller 415 connected to the water quality sensor 405. The controller 415 also controls the pump 416. Upon expiration of the first stage 410A, the controller allows the preparation to continue until a certain amount of fluid is collected in batch container 417, preferably an amount required for a treatment. Once this threshold quantity is delivered, the controller will not allow the pump 416 to be started until the filter module 425 is exchanged with a fresh one. The second stage filter 410B, preferably, is sized to ensure that, by itself, it can purify at least a single batch of water, plus a safety margin without any contaminant breakthrough to the output line 404. In a preferred embodiment, the second stage filter 410B is a smaller size than the first 410A. In the preferred embodiment, the second stage filter 410B may be of a different type which may not be as able to handle high contamination loads as the first 410A. This may be acceptable because, although after breakthrough is detected, the emerging fluid is still substantially purified and the load input to the second stage filter 410B may remain low until a single batch of fluid is prepared.

In an alternative embodiment, the filter module 425 is provided with a permanently attached data carrier 423 such as radio frequency identification device (RFID), bar code (1- or 2-dimensional), contact-type identification device, etc. The data carrier 423 contains a unique identifier of the filter module. When a cartridge is connected to the pump, the controller 415 reads the data carrier 423 using a reader device 422 and stores the identifier in a memory 437. If the water quality sensor 405 indicates contaminant breakthrough, the controller permanently stores the identifier in an expired directory in the memory, which has a non-volatile portion for the directory. If a user attempts to connect a module 425 with an identifier stored in the directory, the controller will not operate the pump and will indicate the error condition by means of an annunciator 420 or equivalent device, such as an LCD display message.

Note that in an alternative device, the data carrier 423 is a programmable device with a writable memory. In this embodiment, the controller 415 programs the data carrier 423 with a flag indicating that the filter module 425 is expired. The controller 415 then prevents the initiation of a new batch.

FIG. 1B also illustrates an optional embodiment with a pressure transducer 435 that may be used to test for clogging of the first stage filter 410A. When the pump 416 head pressure reaches a particular maximum, in order to allow a batch preparation to be completed, the controller activates a normally-closed valve 426 to bypass the first filter stage 410A. Water flows through a bypass line 427 and through the second stage filter 410B. The expiration of the filter module 425 may then be enforced by the controller in either of the ways described above. The above embodiment may be used in filter modules 425 that contain filters that clog when depleted such as carbon filters or porous membrane filters. Not that the clogging and breakthrough devices described above may be combined or used exclusively in a given filter module embodiment. Note also that the head pressure may be sampled and stored over a period of time to determine if the pressure change profile is characteristic of a filter suffering normal usage. This would distinguish, for example, an accidental line blockage and prevent inappropriate use of the bypass line 427.

Figure 2A:
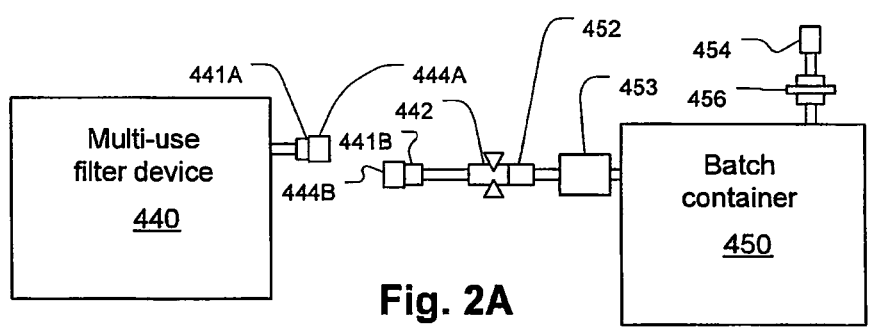
FIGS. 2A and 2B illustrate a filter and batch container with connector systems that ensure against contamination.
Figure 2B:
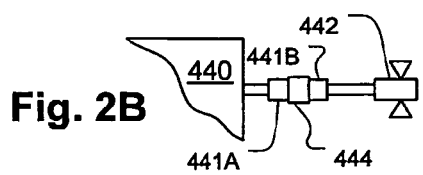

Referring to FIGS. 2A and 2B, a multi-use filter device 440 has an outlet port 441A with a cap 444A to avoid contamination. The outlet port 441A is connectable to a mating port 441B, which is also capped (cap 444B). The ports 441A and 441B may be, for example, locking luer connectors. A special clamping connector 442, which seals itself when disconnected from a mating connector 452 is connected to port 441B and a line connecting it to a batch container 450 which receives purified water from the multi-use filter device 440. A microporous filter 453 guards against the introduction of contaminants by touch contamination when connectors 441A and 441B are mated.

Figure 3:
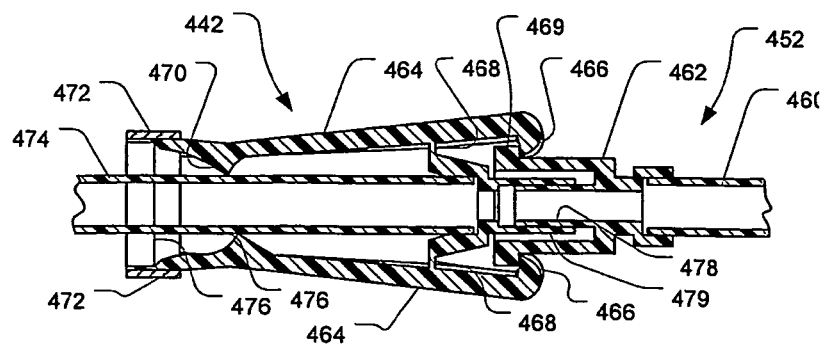
FIG. 3 illustrates a self-clamping connector.

The special clamping connector 442 may any suitable device that seals off, to prevent contamination. An embodiment of such a connector is shown in FIG. 3, although the sealing and disconnecting functions, to be described below, can be performed by separate mechanisms so this embodiment is not essential. An outlet tube 460 connectable to the filter 453 of FIG. 2A is permanently affixed to a male luer fitting 478 of a male connector 452 that is received by a female luer fitting 479 of a female connector 442. The female connector 442 has a pair of latch arms 464 that engage a ridge 469 of the male connector 452. The latch arms 464 pivot on living hinges 468 affixed to the female luer fitting 479. Pinching ridges 470 and 476 compress the tube 474 when a bendable retaining ring 472 is squeezed. At the same time, engaging ends 466 of the latch arms 464 retract from the ridge 469 releasing the male luer connector 452. The bendable retaining ring 472 retains its deformed shape once it is pinched so that the tube 474 remains pinched and thereby sealed when the connectors 442 and 452 are disconnected. The bendable retaining ring 472 may be made of ductile metal, for example. The retaining ring 472 may be replaced by another suitable device such as a ratchet mechanism.

Returning to FIGS. 2A and 2B, when the multi-use filter device 440 is first used, its outlet connector 441A is sealed with a cap 444A as is the inlet connector 442 (with cap 444B) of the batch container 450. The batch container 450 may be sealed and sterilized with the special fitting 442 and its mating connector 452, which may correspond to elements 442 and 452 in FIG. 3, connected in a completely sealed and presterilized state. Other ports such as a sampling port 454 may also be sealed and, if only used as outlets, protected from intrusion of fluid by means of a check valve 456 and/or another membrane filter 453 (not shown separately). The first time the batch container 450 is connected to the multi-use filter device, the caps 444A and 444B are removed and the connectors 441A and 441B mated. After filtered water is collected in the batch container 450, the special clamping connector 442 is disconnected and left connected to the multi-use filter device 440 to keep it sealed and free from contamination as shown in FIG. 2B. The second time the multi-use filter device 440 is used, the special clamping connector 442 is removed by means of the connector pair 441A and 441B and discarded while a new batch container's 450 connector 441B is mated to the pre-existing multi-use filter device's 440 outlet connector 441A. The connector 441B carries a new special clamping connector 442 and the same process can be repeated.

Figure 4:
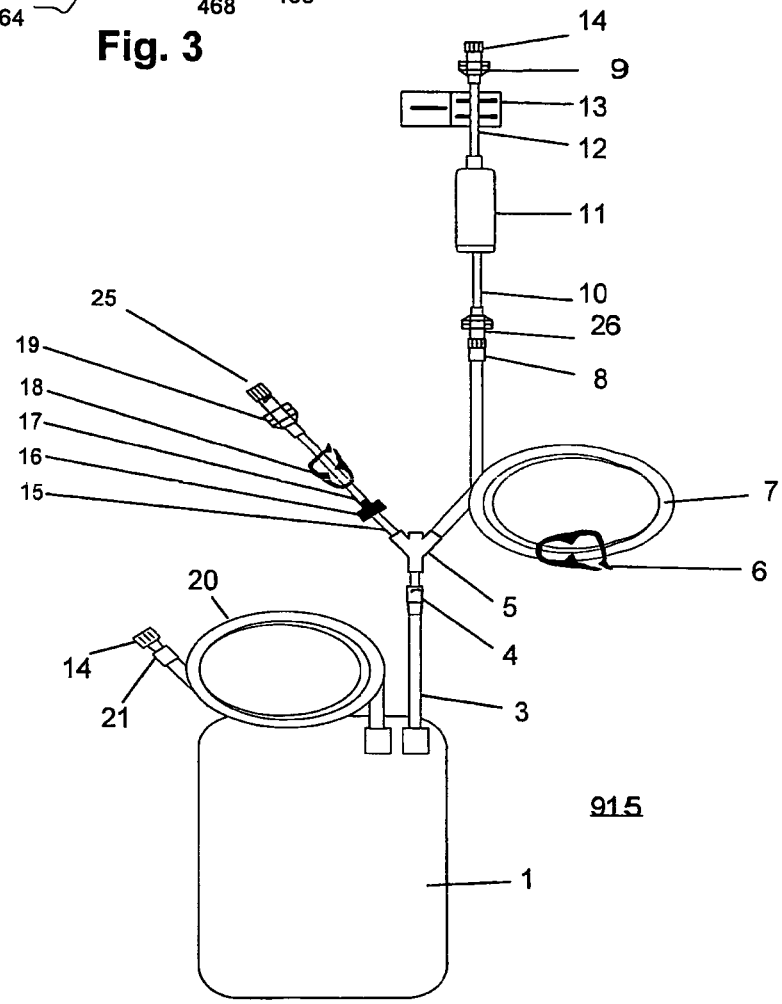
FIG. 4 illustrates a batch container tubing set.

FIG. 4 shows an embodiment of a batch container, for example one that may be used with the foregoing embodiments, but in particular, with the above embodiments. The batch container 1 has a batch container, proper, 1, a break-off female luer lock connector 4, a y-connector, 5, a pinch clamp 6, a male luer 8, a female luer 26, a sterile filter (e.g., 0.22 micron pore or pyrogen filter) 11, a non reopenable tubing clamp 13, a non-breathing cap 14 on a female luer 9. Line 15 has an in-line check valve 16, a pinch clamp 18, a break-off male luer cap 25 and female luer 19, and a female luer 21. Various tubing branches 3, 7, 10, 12, 15, 17, and 20 connect these elements. The batch container 1 is delivered to a patient treatment setting as a sealed sterile container with all terminals sealed. The batch container 1 may contain, as delivered, a concentrate solution sufficient to create a treatment batch of fluid, such as dialysate or replacement fluid, when water is added. Concentrate may be added by means of the luer connector 21. In the tubing set delivered to the treatment site, the tubing branch 20 may be sealed and cut after the concentrate is added. Water is added at the treatment site through connection to a water source via luer 9. The water is preferably metered to provide a predefined quantity. The sterile filters should be sufficient to protect against contamination by pyrogens before water is added to the batch container 1. A sample of diluted treatment fluid may be drawn through the luer 19 before treatment. The check valve 16 prevents any contamination due to backflow from the sampling procedure. After water is added to the treatment fluid container 1, the luer 9 is disconnected from the male luer 8 and the male luer connector connected to the blood treatment system. Luer connectors are shown by way of example as are other features and these are not essential to all embodiments.

Figure 5:
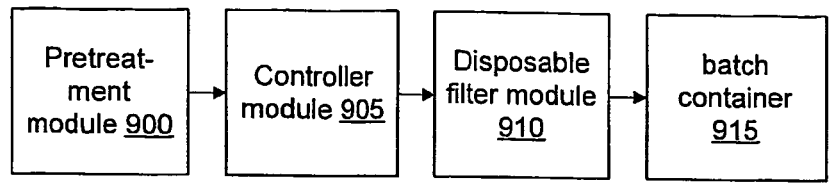
FIG. 5 illustrates a fluid preparation apparatus embodiment in a figurative way for discussing various features and arrangements of a water purification system.

FIG. 5 illustrates another arrangement of a particular embodiment whose description follows. A pretreatment module 900 provides primary filtration from a raw water supply, for example tap water and feeds prefiltered water to a controller module 905 which provides various control functions, a pump, pressure detection and control, and permanent filtering capabilities which are not shown separately here. Water is metered by the control module into a consumable disposable module 910 which may provide deionization, adsorption filtration, microporous filtering, chemical pretreatment, etc. and any other types of filtering that may require replacement of components. The purified water is finally conveyed to the batch container circuit 915 discussed with reference to FIG. 4.

Figure 6:
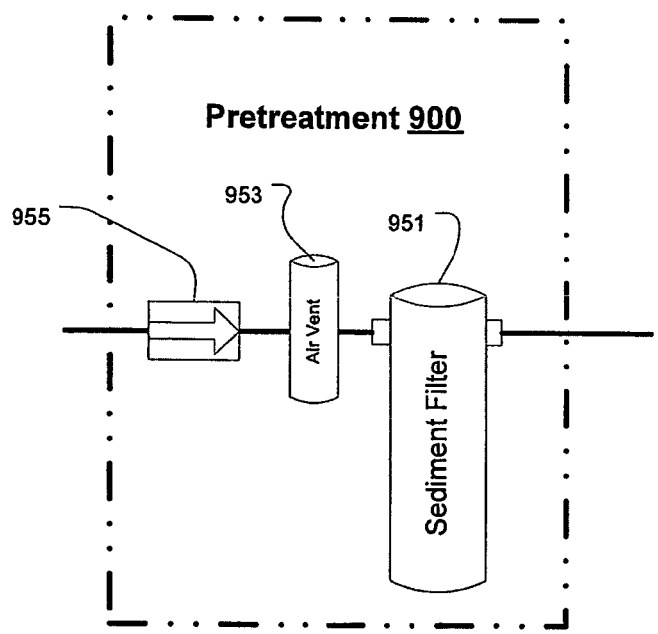
FIGS. 6, 7, and 8A illustrate portions of an embodiment of a fluid preparation apparatus.

Referring to FIG. 6, pretreatment module 900 is shown in more detail. A check valve 955 prevents backflow. An air vent 953 removes air from the primary supply and a sediment filter 951 (which may be replaceable) provides substantial filtering of solids.

Figure 7:
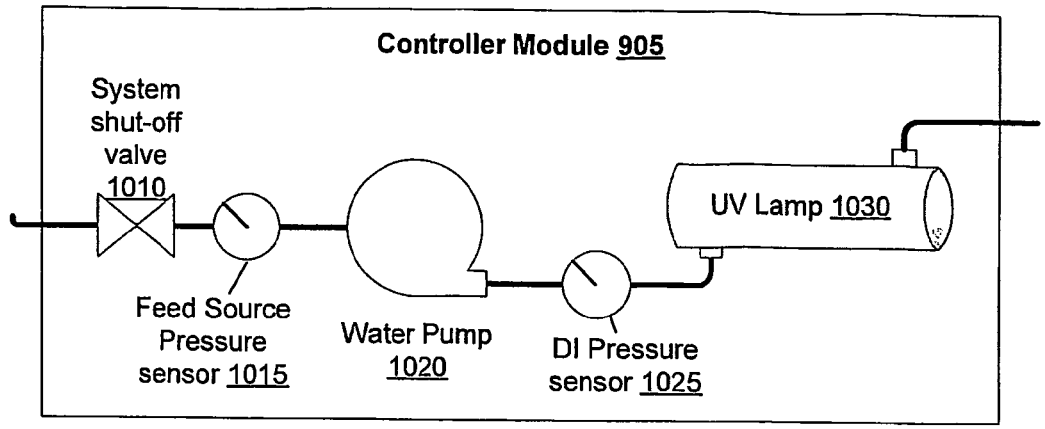

Referring to FIG. 7, the control module 905 is shown in greater detail. A shutoff valve 1010 is provided for safety. Pressure indicators 1015 and 1025 may be provided for monitoring the respective pressures in and out of a pump 1020. Feedback regulation may be provided to ensure that consistent metering is provided if the pump is relied upon for measuring the total quantity of water supplied to the batch container 1. A high intensity ultraviolet (UV) lamp 1031 provides a both sterilization mechanism and a mechanism for removing chlorine and chloramines. Preferably, the UV lamp 1030 is of such intensity and wavelength as to provide disintegration of chloramines. In a preferred embodiment, the lamp is characterized by a 245 nm wavelength and an output power of 750 mJ/cm$^2$ up to 1500 mJ/cm$^2$ which is sufficient to remove chloramines. By oxidizing chloramines and subsequently, as described below, filtering using a deionizing filter, chloramines can be removed.

Note that pressure indicators 1015 and 1025 may be pressure transducers that feed control signals to a control device such as discussed with reference to FIG. 1B and to be discussed with reference to FIGS. 13A and 13B. The operation of pump 1020 may be controlled in dependence on pressure indications from such transducers. For example, if a high head pressure is indicated, an alarm may be indicated and the pump shut down. This may indicate a problem with a connected filter. Also, the pump may be operated for a short interval and a pressure decay profile recorded and compared with an expected decay profile. If the profile does not match, it could be used to indicate a leak (such as in a filter or line) or a clog in the system. If the upstream pressure goes low, it could mean that the water supply is turned off or some other fault. Each of these events may be indicated by means of an annunciator or display (e.g., see 330 and 380 at FIGS. 13A and 13B and attending discussion) and/or by switching off the pump to avoid damage to the system and to notify the operator to take corrective action.

Figure 8A:
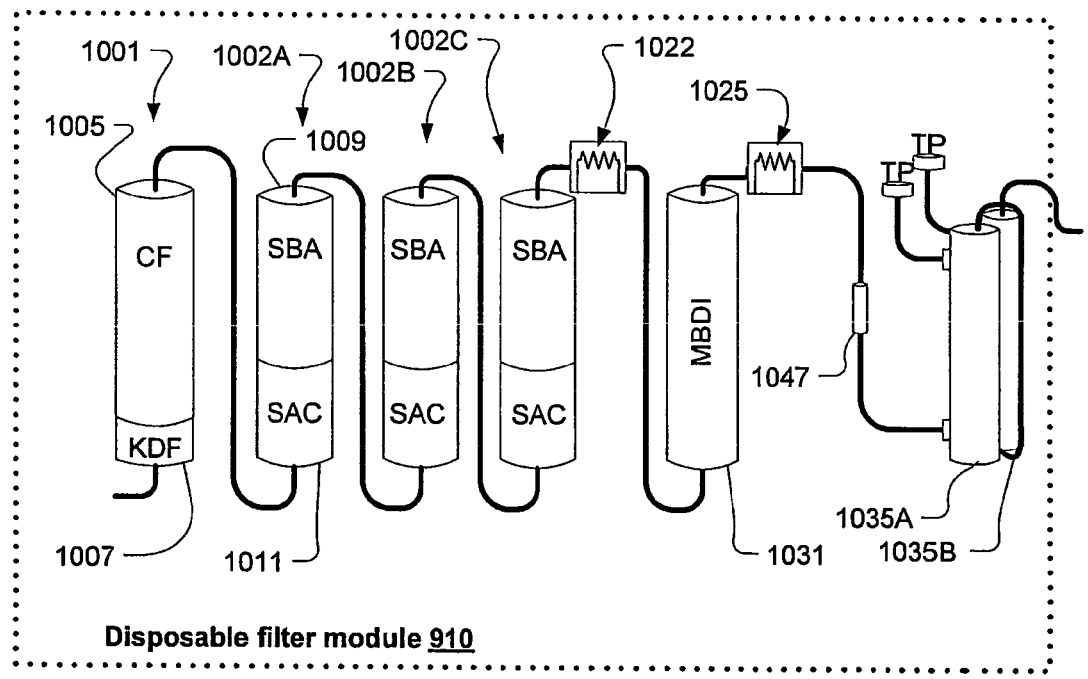

Referring to FIG. 8A, the replaceable (disposable or remanufacturable) filter module 910 contains a first stage filter 1007 copper-zinc alloy which is used to subject the water to a reduction/oxidation process to remove ions. This removes ions through a chemical reaction. An embodiment is KDF 85 media where about one pound is used for a flow rate of 150 ml./min water flow rate. A activated carbon filter 1005 follows which is a well-known adsorption type filter. Next three stages of strong acid cation (SAC) 1011 and strong base anion (SBA) 1009 filters follow in series. The SAC/SBA filter cartridges 1011/1009 are not mixed beds as typically used in water filtration applications. They separate the cation and anion stages as illustrated because it has been determined to be much more effective at removing colloidal aluminum from the treated water. Note that the order of the SCA and SBA beds is not limited to what is shown and that they can be housed in a single canister or multiple canisters. Also note that other components can be sequenced differently as well as should be clear from this disclosure. For example, it should be clear that the pump 1020 can be used in a pushing arrangement to draw water through the UV lamp and the particulars of the arrangement are not limiting to the inventions disclosed. Also note that the resistivity probe 1022 can be included within a single deionizing filter between previous and following deionization stages and employed to similar effect. In such an embodiment, a deionizing filter would have leads or contacts to connect the probe to an external measurement device or controller.

Note that instead of using layered beds in a single cartridge as described, separate cartridges each containing one of a SBA and SAC filter bed may be used. Also, each cartridge could contain more than one layer of each to provide similar results.

The resistivity probe 1022 detects ion concentration by contact testing of the resistivity of the water. A signal is generated to indicate that this will be the last allowed batch before the system will require the replacement of the replaceable module 910. Control may be provided as in the embodiment of FIG. 1B, discussed above. The second filter in the present embodiment, which backs up the first stage suffering from breakthrough, is a mixed bed deionization filter 1031. This ensures that the current batch can be completed. A second, final safeguard resistivity or conductivity test is provided with an audible alarm at 1025 as a back up safety measure. If the value it detects is above a certain level, the pump 1020 may be shut off and an alarm sounded. This may come into play if the resistivity probe 1022 fails, or if the safeguards discussed with reference to FIG. 1B are breached. TP is a hydrophobic membrane air vent which allows air in ultrafilters 1035A and 1035B to be purged. The ultrafilters 1035A and 1035B may be a microtubular filter such as used for dialysis. An air vent may also be provided as shown at 1047. The air vent may, for example, have a 1.2 micron hydrophilic membrane that blocks air. There is a hydrophobic membrane port which allows air to vent from the filter. These are available as off the shelf components. Any suitable air elimination device may be used and these features are non-limiting of the described embodiments. Also, the second stage MBDI type filter 1031 can be a layered deionization filter such as 1002C with the same benefits as described in terms of providing protection against breakthrough. Also, the final resistivity sensor 1025 can be located as shown or moved to another location downstream of the final deionization stage, such as after or between the ultrafilters 1035A and 1035B, and the configuration shown is not limiting of the invention.

Note, it should be clear that resistivity probe 1022 may be used in a configuration such as that of FIG. 1B, with the resistivity probe 1022 corresponding to sensor 405 such that filter module 910 corresponds to filter module 425.

Note that two separately-housed ultrafilters 1035A and 1035B are serially interconnected. The separate housings ensure against failure mechanisms such as grow-through of pathogens, adjacent simultaneous or shared seal failure. For example, prior art reference US Patent Publication No. 2004/0105435, cited in the Background section, shows a filter cartridge with two microporous membranes in adjacent layers of a filter cartridge housing. These may share a seal mechanism or adjacent seals such that failure of the seal of one necessarily involves failure of the seal of the other. Also once a grow through problem occurs in one, the adjacency may cause the problem to creep directly into the adjacent membrane. These problems are prevented by the illustrated arrangement of separate redundant ultrafilters.

Figure 8B:
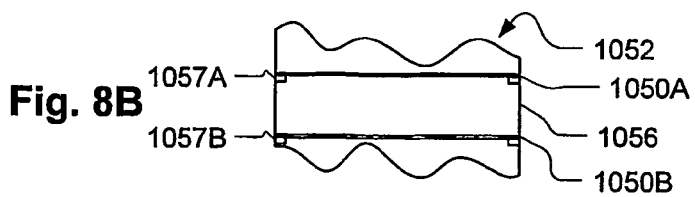
FIG. 8B illustrates a portion of a filter module in which two redundant ultrafiltration membranes are commonly housed.

Note that the benefit of separately housed filters may be substantially provided in a single housing by substantially separating two ultrafilter layers. Referring to FIG. 8B, for example, a multilayer filter with various types of filter elements housed in a common cartridge 1052 contains two ultrafilter layers 1050A and 1050B. The cartridge may be as described in US Patent Publication No. 2004/0105435, which is hereby incorporated by reference as if fully set forth in its entirety herein. The two ultrafilter layers 1050A and 1050B, separate membranes, are kept apart my an intermediate layer 1056, which may be a spacer or another filter medium. Separate seals 1057A and 1057B, which are also spaced apart, are provided.

Note the final conductivity/resistivity sensor/alarm 1025 may control the pump, as noted. A controller 1090 may be connectable to the disposable filter module 910 and configured to stop the pump 1020. The trigger resistivity safety level to cut-off the pump 1020 may be 1 megohm, but may be raised to 2 megohm to allow the use of required temperature compensated resistivity probes (an FDA & AAMI requirement) This does allow use of low cost in-line resistivity probes in the disposable filter module 910.

Preferably, the filter module 910 as well as the modules of other embodiments are of such a flow rate that upward flow of fluids is possible. Generally, prior art deionization beds suffer from the problem of floating or loosening resin particles which may have been disturbed during handling. The separation and floating of the particles breaks up the beds and renders the filters less effective. To avoid this, generally, filter systems are configured to direct flow downwardly through the beds to help keep and compress the resin particles. But if flow rates are kept low, as may be done in the present system, water may be flowed in an upward direction which helps to eliminate air from stream. Air is a notorious problem in the preparation of medicaments such as dialysate. The precise flow rates needed to allow upward flow will vary according to the characteristics of the system. One way to allow faster flow rates without being hampered by break away resin particles is to provide a bed compressor of resilient porous material to compress the bed. Referring momentarily to FIG. 12, in a filter cartridge 1150, a resilient compression layer 1140 urges the filtration material 1145 in a downward direction. The resilient compression layer may be any suitable polymeric or rubberlike material that is compatible with the application.

The following is an example procedure for using the devices discussed with reference to FIG. 4.

1. Remove the dialysate concentrate tubing set 915 and remove the cap 14 from the tubing line 7 that contains the filter 11. (The 0.22 micron filter 11 provides additional protection from inadvertent contamination.)

2. Connect the outlet line 404 to the concentrate bag luer connection 9.

3. Break the frangible luer connector 4 which connector is configured to form a permanent seal on the side facing the Y-junction 5 when disconnected.

4. Add predetermined quantity of water into the concentrate bag using the purification plant through tubing branch 7 through luer connector 9.

5. Optionally a user can write on the bag label the date and time water was first added to the concentrate bag, to assist in ensuring that it is used within a period of time. An automated scheme may be employed as well.

6. Shake the batch container 1 well to mix.

7. Confirm solution conductivity prior to use. Remove the break-off cap 1 and draw sample from this branch 15. After removing the sample, clamp the line using the pinch clamp 17 provided.

8. (The following is normative according to a preferred embodiment and not limiting of the invention) Conductivity must be in the range 13.0 to 14.4 mS/cm. Nominal conductivity for the dialysate solution is 13.7 mS/cm at 25° C. If conductivity does not meet this specification do not use it. Verify that the results are accurate. If conductivity is high additional water may be added to bring it within specification. If conductivity is low then the solution must be discarded.

9. Using the non re-opening clamp 13 provided, clamp the line that is connected to the water purification plant.

10. The clamp 6 is, next, clamped on the line that is connected to the dialysate bag 1.

11. Disconnect the water source at the luer connection 26.

12. Connect the bag of dialysate solution to the dialysis circuit at the connection 8. This leaves the filter 11 and permanent clamp 13 in place to protect the water supply source.

13. Unclamp the line going to the dialysate bag using clamp 6, and initiate treatment after verifying that dialysate will be used within 24 hours from when water was added.

Figure 9A:
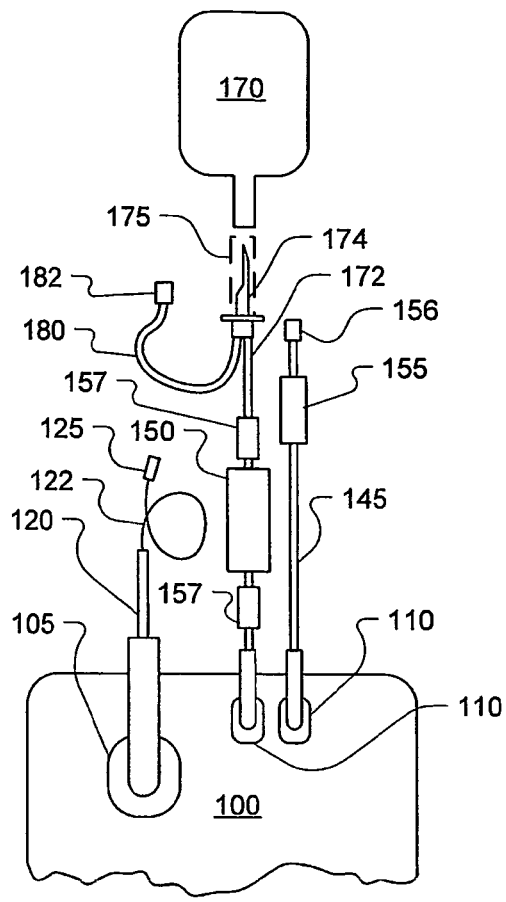
FIGS. 9A and 9B illustrate embodiments of a batch container.
Figure 10A:
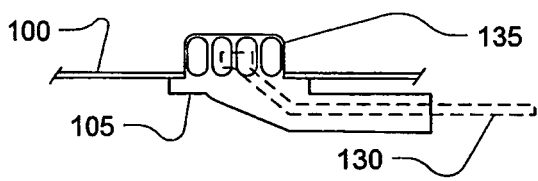
FIG. 10A illustrates a fluid quality sensor such as a conductivity or resistivity sensor configuration for sensing fluid quality in a container.

Referring to FIGS. 9A and 10A, a batch container 100 has a fluid quality sensor 135 of a probe 120, such as a contact-type conductivity sensor. The latter may simply be two metallic surfaces separated by a known distance and of a given area that has been calibrated. A cage 135 in a support 105 sealed to the wall 130 of the batch container 100 which may be a polymer bag as typically used in the medical industry. The cage 135 prevents an opposing wall (not shown separately) from preventing fluid from circulating around and through the cage and in contact with the probe such that a reading of the probe 120 is improved. The probe 120 extends from the support 105 and has a lead 122 with a signal connector 125 that can be connected to a controller (discussed later). The probe 120 is an independent element and can be used with any of the embodiments so its description here in combination with other features is not intended to be limiting. Note that preferably, the probe assembly is permanently sealed to the batch container such that there is no possibility that contaminants can enter the batch container 100 interior.

At 110, a fitting connecting a sample or feed line 145 is shown. The latter may be used, with a connector 156, connect a sampling syringe to draw out a sample of a medicament or infusate. A check valve may be provided at 155 to prevent ingress of contaminants. A clamp (not shown separately) may be provided as well to guard against contamination. In an alternative embodiment, line 145 may be configured for injecting a soluble concentrate into the batch container 100 before the container 100 is sealed and sterilized as a unit (for example, by gamma ray sterilization). When a prescribed quantity of purified water is added to the batch container, the diluted concentrate may form a medicament or infusate such as replacement fluid for hemofiltration or a dialysate for hemodialysis. Line 145 may also represent a draw line that may be connected to a treatment machine. In the latter case, a sterile filter (at 155), such as a microporous membrane of 0.2μ may be provided to guard against touch contamination. Additionally, a clamp may be provided as at 155.

In the embodiment of FIG. 9A, purified water may be added to the batch container by another instance of a line similar to 145. Alternatively, if concentrate or other medical solute or medication is contained in a separate container, such may be added to the batch container 100 by means of a double lumen spike 174. (Details of a suitable dual lumen spike can be found in US Patent Publication No. 2004/0222139, which is hereby incorporated by reference as if set for in its entirety herein). A spikable bag 170 contains, for example, medical fluid concentrate such as concentrated dialysate. Purified water is pumped through connector 182 of line 180 and passed into the bag (after spiking) by the dual lumen spike 174. The fluid circulates in the bag carrying its contents back through the dual lumen spike 174 through line 172, through a filter 150 into the batch container. The dual lumen spike may be sealed by means of a removable cap 175 so that the batch container and fluid lines can be sealed and sterilized and later delivered as a unit without contamination. Clamps 157 may be provided to seal the batch container 100. A special clamping connector 442 may be provided and used as discussed with reference to FIG. 1B in line 180. If concentrate is present in the batch container 100 rather than using a spiking bag 170, the concentrate may be used to obtain a data point for a calibration line fit for measuring fluid conductivity.

Figure 9B:
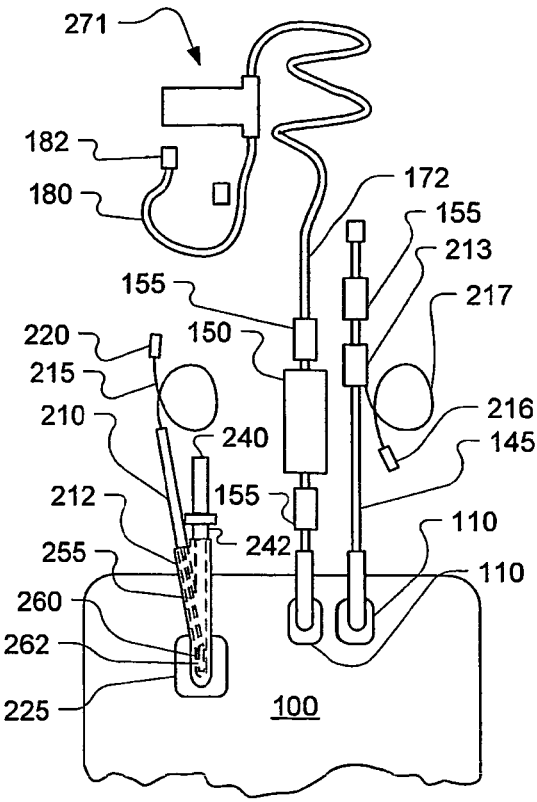

Referring to FIG. 9B, instead of providing a conductivity or resistivity sensor in the batch container 100, a dual lumen takeoff 255 with a common lumen (Y-configuration) 260 housing a water quality sensor 262 of a probe 210 with corresponding signal connector 220 and lead 215. A syringe port 240 and check valve 242 are connected inline to the other branch of the Y-junction. When a syringe (not shown) is attached and fluid drawn into it, fluid from the batch container passes over the water quality sensor to allow its quality to be measured. In other respects the elements of FIG. 9B are the same (and identically numbered) as those in FIG. 9A.

Referring to FIG. 11, a replaceable multiple use filter module 1125 as may be used in the various embodiments described herein has an inlet port 1130 and an outlet port 1110. A physical arrangement of filter cartridges 1111 is shown which provides for a compact module 1125 that is advantageous for packaging and assembling to a chassis (as discussed relative to FIGS. 13A and 13B). Tubing 1116 runs from the top of each cartridge 1111 to the bottom to provide upward flow as discussed earlier. A signal port 1100 for reading fluid quality sensors 1115 and 1105 is provided in a housing. 1127. Signal port 1100 may have a lead wire and connector installed to it or one may be provided separately. Alternatively, signal port 1100 may be a wireless port powered by a battery. Signal port 1100 may include a data carrier as discussed with reference to FIG. 1B or a data carrier may be provided separately or without the signal port if a fluid quality sensor is not provided.

A data carrier may include software and instructions for using the filter module 1125. These may be read by a permanent component of a filtering system as described in connection with FIGS. 13A and 13B. A base unit 335 may be configured substantially as described with reference to FIG. 5 with the base unit 335 housing the components of the permanent pretreatment module 900 and controller module 905. The base unit may contain a display 330, such as an LCD display. Instead of, or in addition to, a display, the base unit (and other embodiments described herein) may have a voice generator or other type of output device. An inlet port 341 may be provided for receiving raw water to be filtered and an outlet port 340 for attachment to a filter module (which may be multi- or single-use) which is received in a locating station 315. The latter may have a reader 311 to read a data carrier or to connect with a fluid quality probe such as one or more conductivity sensors described above. A further locating station may be provided such as 305 for a batch container. This may have a data carrier reader 320 and/or various other components (at 321) such as a heater, a mixer, such as a moving field generator for magnetohydrodynamic mixing of the contents of an installed batch container. The base unit 335 may have a port 310 for connection to a fluid quality probe of the batch container. This may provide a calibration input as well as a final measurement of fluid quality. The embodiment of FIG. 13B additionally provides a locating station for a concentrate container such as 170 described with reference to FIGS. 9A and 9B. The base unit 335 may further be fitted with a controller containing a computer with a connection to the Internet or other network connecting the base unit with a server 390.

In an embodiment, features indicated at 301-306 may be added to allow the base unit 335 to control when and whether an outlet line of a batch container should be opened and clamped. A batch container is fitted in the station 305 and an outlet line of the batch container fitted between clamping portions 303 and 304. A detector 306 verifies that the line has been fitted in place. When the system is run, an actuator 302 and motor 301 may be activated to clamp the line during fluid purification and as the batch container is filled. After the batch is filled, the clamp may remain closed until a treatment operation, which may be run while the batch container remains in place, is begun. At treatment time, the clamp mechanism 303 and 304 can enforce the expiration time of the batch of fluid. For example, a timer can be started within the controller of the base unit or, equivalently, a time/date stamp stored and the clamp only released if the batch of fluid is used for treatment within a certain period of time. For this purpose a treatment machine and the base unit 335 may be combined into a single device under common control or the two may be linked by a data link to operate cooperatively to achieve such a result. The flow chart of FIG. 15 describes the control steps involved.

Figure 10B:
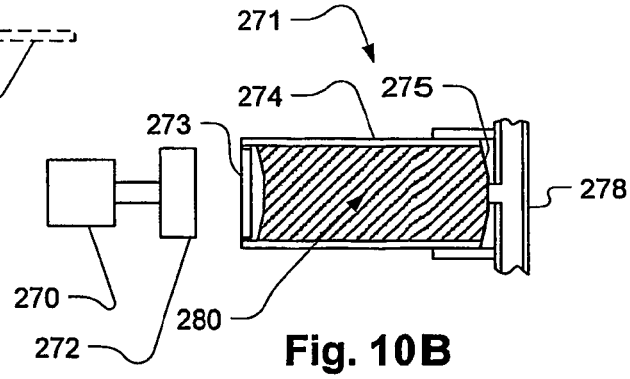
FIG. 10B illustrates a medicament concentrate cartridge.

Referring now to FIGS. 9A and 10B, instead of a concentrate container in the form a spikable bag 170 as illustrated in connection with FIGS. 9A and 9B, a cartridge 271 as illustrated in FIG. 10B may be used. Here, concentrate 280 is within a sealed cylinder 274 with a piston 273 and a burstable seal membrane 275. The cartridge may be fitted in the base unit 335 (FIGS. 13A and 13B) which may contain a linear drive 270 and plunger 272 to push the piston 273 thereby bursting the seal membrane 275 and inject contents into a T-junction 278 in the path of purified water sent into the batch container 100. Note that the cartridge 271 may be provided as part of the sterile batch container fluid circuit shown in FIG. 9B.

Figure 15:
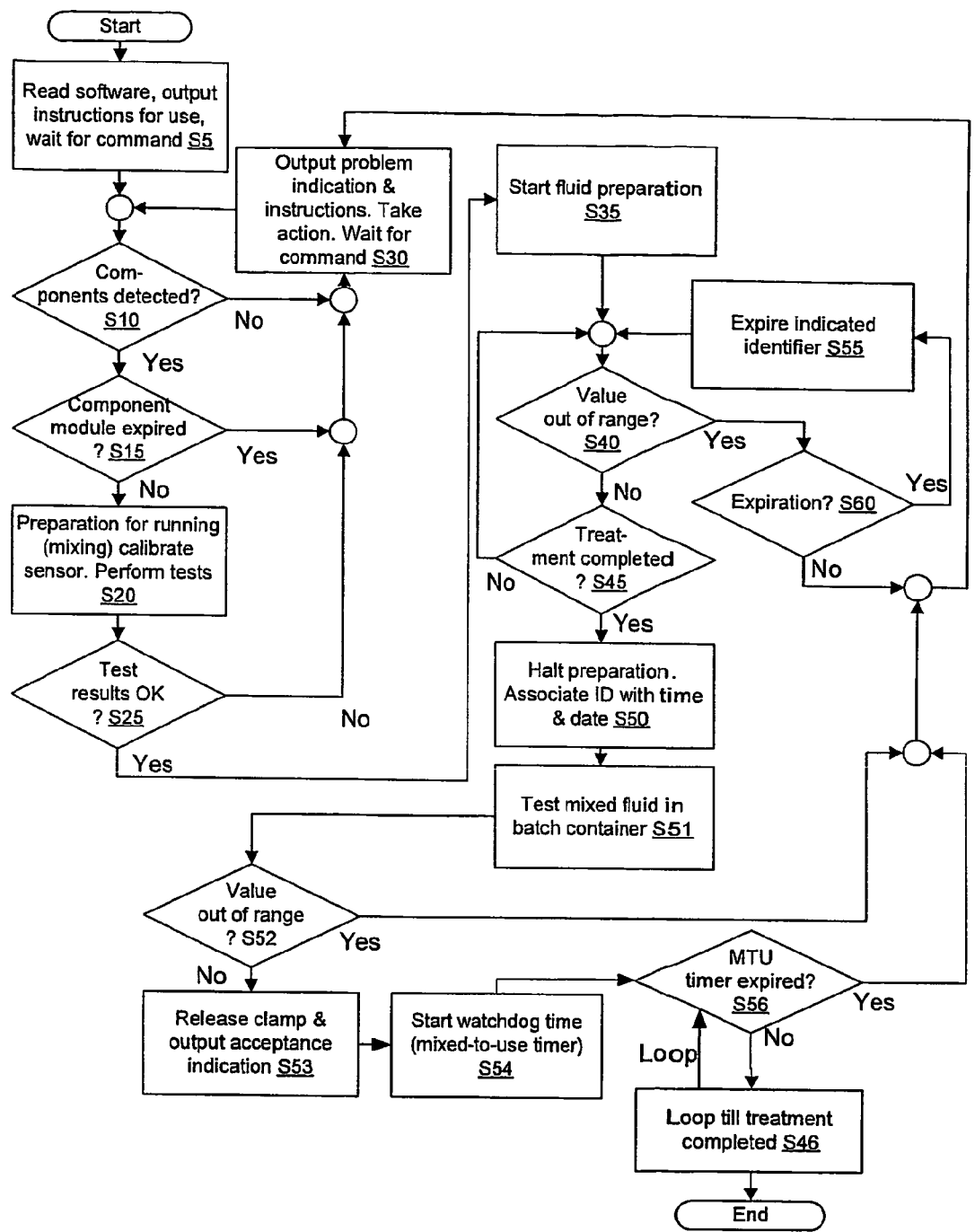
FIG. 15 is a flow chart for discussing various control options of the various embodiments discussed herein.

Referring to FIGS. 14 and 15, the base unit 335 and corresponding parts of other embodiments described herein, may contain a programmable controller including an embedded computer 600 with memory, non-volatile storage, communication elements, etc. Various sensors 605 such as discussed in connection with various embodiments may be connected to provide input to the controller executing a program stored in memory. The latter may stored in firmware or obtained from a data carrier via a data port 610 as described previously. In addition, a network or Internet connection to a server 625 may be provided to obtain and transmit data such as software, instructions for use, expired identification codes, etc. Actuators 615 such as valve clamps, pumps, and annunciators 620 such as alarms may be provided as well.

A sample program for operating the various embodiments described herein is shown in FIG. 15. The process may begin with firmware until software loaded at a later stage takes over. Software may be read from a data port or data store and instructions for using the system output at step S5 whereupon the system waits for user input. The instructions may indicate to press hard or soft key to continue at which point steps S10 and S15 are executed to determine if a no-go condition exists. If a necessary component (S10) has not been connected, step S30 will be executed and the system may output an appropriate message to instruct the user to take corrective action and wait for response. Similarly, if in step S15, it is determined that a component is expired, such as a batch bag that has been previously used or a filter module has been used and previously indicated as having suffered breakthrough, step S30 will be executed. At step S20, various system tests may be performed such as a pressure profile test or quality test. Tests may also include determining if the conductivity indicated by a connected conductivity probe is within specified limits. In step S25 it is determined if all tests have been passed and control passes to step S35 where fluid preparation is begun. If not, step S30 is performed and appropriate output is generated on a display such as 330. If a value goes out of range at step S40, control passes to step S60 to determine if an expiration event has occurred, for example, breakthrough of contaminants in a filter module. Note that Filter modules may be "stamped" with a permitted time of use after a first use when presumably the seal was first broken. This may be enforced in the same manner as discussed with reference to attempted reuse of a filter module after breakthrough was detected. Thus, step such an event may be detected at step S60 as well.

At step S55 depending on the type of data carrier (e.g., programmable or just carrying a unique ID), the expired or spent unit is indicated as expired so that reuse can be prevented. For example, in S55 the data carrier may be programmed with a token to indicate that the attached filter module is expired or a server may be sent a message to indicate that its unique ID should be added to a list of expired IDs. Any suitable device may be used to "expire" a unit. Since expiring a unit may still allow a batch to be prepared, control returns to S40. Completion of the treatment may be determined at step S45 by measuring the total mass pumped or by other means. For example, if the embodiment provides a conductivity probe in the batch container, step S45 may depend on the measured conductivity of the batch contents. Once completion is determined, the system may be halted at step S50 and the batch bag "stamped" with a time and date. Note that further instructions may be output at this point.

In one embodiment, the water purification and treatment may be done from a single apparatus and under common control. The steps following step S50 illustrate this. Assuming purified fluid has been added to a batch container of some description such as those described in the current specification or some other, the contents of the container may be mixed, if a solute is involved, and the contents checked in some way in step S51. For example, the conductivity of a mixed batch or the resistivity of a pure batch can be checked determine its conformity with treatment specifications. In step S52, if a value is out of range, control passes to step S30, but if not, the batch may be utilized at any time up to an expiration time/date (MTU time, or Mixed Till Use-time). In step S53, an outlet clamp that prevents fluid from being drawn from the batch container is released to allow a treatment to be performed with the fluid product. At the same time; an acceptance message can be output to the user on a display. At this time, in S54, a time stamp is stored or a timer started to keep track of the expiration of the batch of fluid. If the expiration is not observed, which is tested at step S56 by checking to see if the timer has expired, the clamp will close in step S30 (under the general step indicated as "take action") and an appropriate message output. The system will then wait until treatment is completed while, optionally, continuously checking the MTU timer in steps S46 and S56.

Note that many of the described mechanical and control features are novel and inventive alone, as subcombinations with other features and their description in combination in the above embodiments is not intended to be interpreted as limiting of the inventions disclosed herein. Referring to FIG. 16, when a treatment machine 700 attempts to use a batch container 710 tagged with an expiration date at step S50, it can determine if the date has passed and prevent use of an expired batch container thereafter. This may be implemented with contact or wireless data reading devices, a programmed smart card type device or via an Internet server as described with reference to the mechanism for enforcing non-reuse of filter modules.

Referring to FIG. 17, air may evolve from fluid as it passes through an ultrafilter 714. Preferably, the ultrafilter 714 has a high membrane surface and in such filters, the potential for air evolution may be fairly high. To avoid problems with bubbles forming in the filter, the embodiment of FIG. 8A shows transducer protectors TP, which are hydrophobic air vents. But the lines leading to them can fill with water and render them useless for air purging. A refinement of the configuration of FIG. 8A, which may be used in any water treatment plant as a final protective stage, is to provide an ultrafilter 714 (which may be a standard dialyzer capped at the lower blood port) with an inlet 712 and outlet 704 on one side of the membrane connected by a return line 704 flowing through an air filter/vent 706, through further line 708 into a T-junction 717 and back into the inlet line 712. Ultrafiltered fluid is drawn out through line 707. Again, the filter/vent 706 may be a 1.2 micron air vent with a 1.2 micron hydrophilic membrane that blocks air and a hydrophobic membrane port which allows air to vent from the filter. These are available as off the shelf components. The water column defined by line 708 is denser than the corresponding column within the housing of ultrafilter 714 so that a return flow will exist through the branch 704, 706, 708. The reason for the lower density is due to the evolution of air in the ultrafilter 714.

An alternative design that integrates air vent configurations into the housing of the ultrafilter 714 is shown in FIG. 17A. For the outlet (filtrate) side of the media, an air vent, e.g., a hydrophobic membrane type air vent 765 may be integrated into the outlet of an ultrafilter 715 and an air filter such as a hydrophilic air filter membrane 766 integrated into the outlet. Any bubbles coming out of fluid collect at the top of the filtrate side (in a header space of a microtubular membrane type filter) and be vented by the hydrophobic air vent 765. On the inlet side of the ultrafilter 715 (the side of the filter media that has not yet been ultrafiltered), air collecting in the inlet side will leave by an air vent 467, for example one using a hydrophobic membrane 469. A check valve 742 may be provided to prevent siphoning and/or reduce risk of contamination.

Referring to FIG. 18, to address any problem with inadequate flow through the return branch of the FIG. 17 embodiment, a resilient channel element 730 such as an inline bladder 731 may be included with check valves 724 and 728. When the system pumps fluid, the resilient channel element 730 stores fluid under pressure and releases it in pumping fashion when the system stops pumping. Again, an air filter/vent 724 allows air to escape and purged from the return line 726. The return flow problem can also be dealt with by replacing the T-junction 717 with a Venturi device configured to create a suction in line 708 by using an accelerated fluid flow through the line 714,712.

One of the drivers for the features discussed above is a need to provide pure water irrespective of input water quality. The above embodiments are not reliant upon water quality and are designed to reliably produce pure water or solutions regardless of input water quality. Various embodiments are also designed to reduce the costs associated with lower volume (10-60 liters) preparation of medical and other pure solutions and to maintain simplicity through the combination of semi-permanent and single-use modules which combine to eliminate the complexities, costs and safety issues associated with maintenance, sterilization, and operation of many other prior art systems.

Although the foregoing inventions have, for the purposes of clarity and understanding, been described in some detail by way of illustration and example, it will be obvious that certain changes and modifications may be practiced that will still fall within the scope of the appended claims. For example, the devices and methods of each embodiment can be combined with or used in any of the other embodiments. For another example, the air vents described can be of any suitable description and need not be membrane type air vents at all, although these are preferred.

What is claimed is:
1. A water treatment plant, comprising:
a first purifying filter adapted to purify an input water stream and output a purified stream;
a first microporous membrane ultrafilter effective to sterilize a water stream connected to receive said purified stream and further filter it;
a second microporous membrane ultrafilter effective to sterilize a water stream connected in series after said first microporous membrane ultrafilter;
said first and second microporous membrane ultrafilters each being contained in one or respective housings and having separate seals to said one or respective housings that are spaced from each other;
said first and second microporous membrane ultrafilters having surfaces that are separated by a predetermined flow path that creates a separation between the first and second microporous membrane ultrafilters,
wherein the separate seals are separated by the predetermined flow path, and
the first and second membranes are separated by a predetermined path length,
wherein the at least one of the first and second microporous membrane ultrafilters has two ports on an upstream side of the membrane thereof, the two ports being connected by a return branch having an inline air removing filter.
2. The plant of claim 1, wherein the first purifying filter includes a deionization filter.
3. The plant of claim 1, wherein the return branch includes a T-junction.
4. The plant of claim 2, wherein:
the deionization filter includes first and second stages with a sensor between the first and second stages,
the sensor is effective for detecting resistivity of fluid passing therethrough, and
the sensor is an electronic sensor that outputs an indication of depletion of the first stage.
5. The plant of claim 1, wherein the first and second microporous membrane ultrafilters contain microtubular membranes, and
the first and second microporous membrane ultrafilters having respective longitudinal axes which are parallel and arranged vertically.
6. The plant of claim 1, wherein the air removing filter has a hydrophobic membrane.
7. The plant of claim 1, wherein the return branch has a check valve.
8. The plant of claim 5, wherein the return branch has a check valve.
9. A water treatment plant comprising:
a first a first purifying filter adapted to purify an input water stream and output a purified stream;
a first microporous membrane ultrafilter effective to sterilize a water stream connected to receive said purified stream and further filter it;
a second microporous membrane ultrafilter effective to sterilize a water stream connected in series after said first microporous membrane ultrafilter;
said first and second microporous membrane ultrafilters each being contained in respective housings and having separate seals to said respective housings;
said first and second microporous membrane ultrafilters having surfaces that are separated by a predetermined flow path that creates a separation between the first and second microporous membrane ultrafilters, wherein the separate seals are separated by the predetermined flow path, wherein the first and second membranes are separated by a predetermined path length, and wherein the first purifying filter includes a deionization filter that comprises first and second stages, the first stage having a capacity that is larger than that of the second stage; wherein at least one of the first and second microporous membrane ultrafilters has two ports on an upstream side of the membrane thereof, the two ports being connected by a return branch having an inline air removing filter.

10. The plant of claim 9, wherein the first and second stages of the deionization filter are constructed as a single unit for simultaneous replacement.

11. The plant of claim 9, wherein the deionization filter further comprises a sensor between the first and second stages, the sensor being configured to detect resistivity of fluid passing therethrough and to provide a signal indicative of depletion of the first stage.

\* \* \* \* \*